(12) United States Patent
Copland

(10) Patent No.: US 11,006,823 B2
(45) Date of Patent: May 18, 2021

(54) METHODS AND SYSTEMS FOR OPTICAL COHERENCE TOMOGRAPHY SCANNING OF CORNEA AND RETINA

(71) Applicant: AMO Development, LLC, Santa Ana, CA (US)

(72) Inventor: Richard J. Copland, Albuquerque, NM (US)

(73) Assignee: AMO Development, LLC, Santa Ana, CA (US)

( * ) Notice: Subject to any disclaimer, the term of this patent is extended or adjusted under 35 U.S.C. 154(b) by 172 days.

(21) Appl. No.: 16/260,018

(22) Filed: Jan. 28, 2019

(65) Prior Publication Data
US 2020/0237211 A1   Jul. 30, 2020

(51) Int. Cl.
| | | |
|---|---|---|
| *A61B 3/10* | (2006.01) | |
| *A61B 3/00* | (2006.01) | |
| *G01B 9/02* | (2006.01) | |
| *A61B 3/14* | (2006.01) | |
| *A61B 5/00* | (2006.01) | |

(52) U.S. Cl.
CPC ............ *A61B 3/102* (2013.01); *A61B 3/0008* (2013.01); *A61B 3/1005* (2013.01); *A61B 3/14* (2013.01); *A61B 5/0066* (2013.01); *G01B 9/02091* (2013.01)

(58) Field of Classification Search
CPC ... G01B 9/02091; A61B 3/102; A61B 3/0008; A61B 3/10; A61B 3/1005; A61B 3/14
USPC ....................................................... 351/206
See application file for complete search history.

(56) References Cited

U.S. PATENT DOCUMENTS

| | | |
|---|---|---|
| 5,777,719 A | 7/1998 | Williams et al. |
| 6,550,917 B1 | 4/2003 | Neal et al. |
| 7,830,525 B2 | 11/2010 | Buckland et al. |
| 7,980,699 B2 | 7/2011 | Neal et al. |
| 8,049,873 B2 | 11/2011 | Hauger et al. |
| 8,534,838 B2 * | 9/2013 | Barth ................... A61B 3/1005 351/215 |

(Continued)

OTHER PUBLICATIONS

McKeague, Marta, Sharma, Priya, Ho, Allen C. "Evaluation of the macula prior to cataract surgery", Current Opinion in Ophthalmology: Jan. 2018—vol. 29—Issue 1—p. 4-8; doi: 10.1097/ICU.0000000000000432 (Year: 2018).*

(Continued)

*Primary Examiner* — William R Alexander
(74) *Attorney, Agent, or Firm* — Johnson & Johnson Surgical Vision, Inc.

(57) ABSTRACT

An instrument includes: one or more scanning mirrors to receive an OCT sample beam and to scan the sample beam in two orthogonal directions; and an optical system to receive the sample beam and provide the sample beam to an eye. The optical system includes: a first lens having a first focal length, disposed along an optical path from the scanning mirror(s) to the eye at a distance from the cornea which is approximately equal to the first focal length, and a second lens disposed along the optical path between the first lens and the scanning mirror(s). The second lens receives the sample beam from the scanning mirror(s) and provides the sample beam to the first lens as a converging beam such that, as the sample beam is scanned, the sample beam passes through a pivot point located along an optical axis between the eye and the first lens.

16 Claims, 11 Drawing Sheets

(56) References Cited

U.S. PATENT DOCUMENTS

| | | | |
|---|---|---|---|
| 9,050,027 B2 | 6/2015 | Uhlhorn et al. | |
| 9,155,464 B2 | 10/2015 | Tanaka et al. | |
| 9,402,540 B2 | 8/2016 | Buckland et al. | |
| 10,085,886 B2 * | 10/2018 | Schuele | A61F 9/008 |
| 10,864,114 B2 * | 12/2020 | Schuele | A61F 9/008 |
| 2011/0149245 A1 * | 6/2011 | Barth | A61B 3/1005 351/215 |
| 2014/0081247 A1 | 3/2014 | Heiberger et al. | |
| 2015/0335477 A1 * | 11/2015 | Schuele | A61F 9/008 606/6 |
| 2015/0371401 A1 | 12/2015 | Wang et al. | |
| 2016/0166147 A1 | 6/2016 | Peschka et al. | |
| 2016/0235292 A1 | 8/2016 | Gramatikov et al. | |
| 2016/0278637 A1 | 9/2016 | Gao et al. | |
| 2016/0338589 A1 | 11/2016 | Carrasco-Zevallos et al. | |
| 2017/0071467 A1 * | 3/2017 | Raymond | A61B 5/0066 |
| 2018/0055355 A1 | 3/2018 | Sarunic et al. | |
| 2018/0085253 A1 * | 3/2018 | Schuele | A61F 9/008 |

OTHER PUBLICATIONS

Betty R. Klein, Emma N. Brown, Richard S. Casden, "Preoperative macular spectral-domain optical coherence tomography in patients considering advanced-technology intraocular lenses for cataract surgery", vol. 42, Issue 4, Apr. 2016, pp. 537-541, https://doi.org/10.1016/j.jcrs.2016.01.036 (Year: 2016).*

Dai, C., et al., "In Vivo Full Depth of Eye-Imaging Spectral-Domain Optical Coherence Tomography," Proceedings of SPIE, Sep. 2011, vol. 8135, Applications of Digital Image Processing XXXIV, pp. 81351I-1-81351I-6.

Shirazi, M.F., et al., "Dual Illumination for Cornea and Retina Imaging using Spectral Domain Optical Coherence Tomography," Proceedings of SPIE, Apr. 2017, vol. 10251, Biomedical Imaging and Sensing Conference, 102511G-1 102511G-3.

Mejia-Barbosa Y., et al., "Object Surface for Applying a Modified Hartmann Test to Measure Corneal Topography," Applied Optics, Nov. 1, 2001, vol. 40 (31), pp. 5778-5786.

* cited by examiner

US 11,006,823 B2

METHODS AND SYSTEMS FOR OPTICAL COHERENCE TOMOGRAPHY SCANNING OF CORNEA AND RETINA

TECHNICAL FIELD

Embodiments of this invention pertain to eye measurement systems and methods, and more particularly, to eye measurement systems and methods can make optical coherency tomography measurements of a cornea and a retina of a patient's eye.

BACKGROUND

Various types of eye measurement instruments and methods are known, including autorefractors, wavefront aberrometers, corneal topographers and optical coherence topography (OCT) systems.

An autorefractor is a computer-controlled machine used during an eye examination to provide an objective measurement of the refractive error for an eye which can be used to generate a prescription for glasses or contact lenses. This is achieved by measuring how light is changed as it enters a person's eye.

Wavefront aberrometry measures the way a wavefront of light passes through the cornea and the crystalline lens of an eye, which are the refractive components of the eye. Distortions that occur as light travels through the eye are called aberrations, representing specific vision errors. Various types of wavefront aberrometers and methods are known, including Tscherning aberrometers, retinal ray tracing, and Shack-Hartmann aberrometers.

Corneal topography, also sometimes referred to as photokeratoscopy and videokeratoscopy, is a technique that is used to map the curved surface of the cornea. Corneal topography data can help measure the quality of vision as well as assist in eye surgery and the fitting of contact lenses. Various types of corneal topographers and methods are known, including Placido ring topographers, Scheimpflug imagers, and more recently, point source color LED topographers (CLT).

Optical coherence tomography (OCT) is a method of interferometry that determines the scattering profile of a sample along the OCT beam. OCT systems can operate in the time domain (TD-OCT) or the frequency domain (FD-OCT). FD-OCT techniques have significant advantages in speed and signal-to-noise ratio as com pared to TD-OCT. The spectral information discrimination in FD-OCT is typically accomplished by using a dispersive spectrometer in the detection arm in the case of spectral domain OCT (SD-OCT) or rapidly scanning a swept laser source in the case of swept-source OCT (SS-OCT).

For example, in SS-OCT a swept (scanning) laser may be employed to produce a laser signal with a linear frequency ramp or "chirp." The swept laser signal (OCT reference beam) is applied to a reference arm or reference path of an OCT interferometer, and also through a sample arm or sample path of the OCT interferometer (OCT sample beam) to an object (e.g., an eye) which is to be measured. Reflections of the laser signal returned from the different surfaces of structures within the object (e.g., eye) in the sample path can be combined with the laser signal output by the reference path to produce corresponding OCT peaks, corresponding to the depths of the different reflection and scattering surfaces within the object being measured, in an OCT signal output by a detector. By scanning the OCT sample beam in two orthogonal directions (x and y directions) the topography of various structures of the eye can also be determined.

FIG. 1 is a schematic drawing of a portion of a human eye 101 which can be used in the explanations below. Eye 101 includes, in relevant part, a cornea 402, an iris 404, a lens 406, a sclera 408 and a retina 409.

Knowledge of the structure of eye 101 is necessary to plan refractive and cataract surgeries for optimal outcomes. Parameters of interest include: anterior corneal radius, corneal thickness, posterior corneal radius, anterior chamber depth, anterior lens radius, lens thickness, posterior lens radius and total eye length. Many of these parameters can be measured with an OCT system, as described above.

In addition, it is beneficial if some information about the health of retina 409 can be determined by the same instrument. For example, if a patient's retinal health is poor, it is inappropriate to implant a premium IOL because the patient would receive no visual benefit for the additional cost.

OCT systems have been used in the prior art to scan retina 409 of eye 101 of a patient so as to perform medical diagnosis.

FIG. 2A shows an embodiment of an OCT scan module 2000A for scanning retina 409 of eye 101 as disclosed by Peschka et al. U.S. Patent Application Publication 2016/0166147 ("Peschka"). OCT scan module 200A illustrated by FIG. 2A comprises a fiber 2001, collimator lens 2002, X/Y scan-unit 2003, retina scan lens 2004, ocular lens 2005, beam splitter 2007, internal fixation lens 2008 and internal fixation target 2009. The solid-line-beam-path in FIG. 2A shows the OCT scan beam path in which a beam is focused on retina 409 of patient's eye 101. The beam can originate from any one of a variety of sources including broadband light Sources with short temporal coherence lengths or swept laser sources and can be introduced into the OCT system via fiber 1. The dashed-line-beam-path in FIG. 1 shows the beam path of for a fixation target (not shown) coupled to the OCT scan beam path via beam splitter 2007 and is then imaged on retina 409 of eye 101 under investigation via ocular lens 2005 to define the viewing direction of eye 101 under investigation during retinal scanning. Light scattered from the sample is collected, typically into the same fiber 1 used to route the light for illumination. Collected sample light is combined with reference light (not shown) to form light interference in a detector (not shown) as described above.

As seen in FIG. 2A, scan module 2000A can scan a large region of retina 409, but is only able to scan a very small area, if any, of cornea 402—typically less than 1 mm.

However, when planning a cataract surgery, it is typically desired to employ the OCT system to obtain information about cornea 402, which requires scanning a much larger area of cornea 402. For example, a primary condition of concern is keratoconus, which is localized thinning of cornea 402. Also, variations of corneal thickness can cause significant posterior corneal astigmatism. This can be measured and the amount of astigmatism ascertained with an OCT system, but not with scan module 2000A described above.

In order to use an OCT system to optionally achieve corneal scanning, Peschka discloses that the scan module 2000A shown in FIG. 2A may be modified to obtain a scan module 2000B shown in FIG. 2B. As shown in FIG. 2B, the retina scan lens 2004 of scanning module 2000A is replaced with an anterior segment scan lens 2010 to switch the OCT system from retinal scanning to corneal scanning. In this configuration, the OCT system can scan cornea 402, but remains stationary, or moves by less than 1 mm typically on retina 409.

So scan module 2000A scans the retina, and scan module 2000B scans the cornea, but neither scan module 2000A nor scan module 2000B can scan both.

In order to realize an OCT system that can be used both for retinal scans and corneal scan, there is a need to provide the OCT system with additional optical-mechanical modules to exchange retina scan lens 2004 and anterior segment scan lens 2010 and to position different lenses precisely in the optical system of the OCT system and adjust the length of one of the reference arm and the sample arm to achieve the corresponding function. However to do this, the complexity and cost of the instrument is greatly increased in order to combine the functions of retinal scanning and corneal scanning.

Thus it is desired to provide an OCT system and OCT method, and a scanning module and scanning method for an OCT system, which can scan a central corneal region and a large enough region of the retina that its health may be determined. It is further desired to provide such an OCT system and OCT method, and a scanning module and scanning method for an OCT system which scan a central corneal region and a large enough region of the retina that its health may be determined with reduced complexity and cost.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Figure 1:
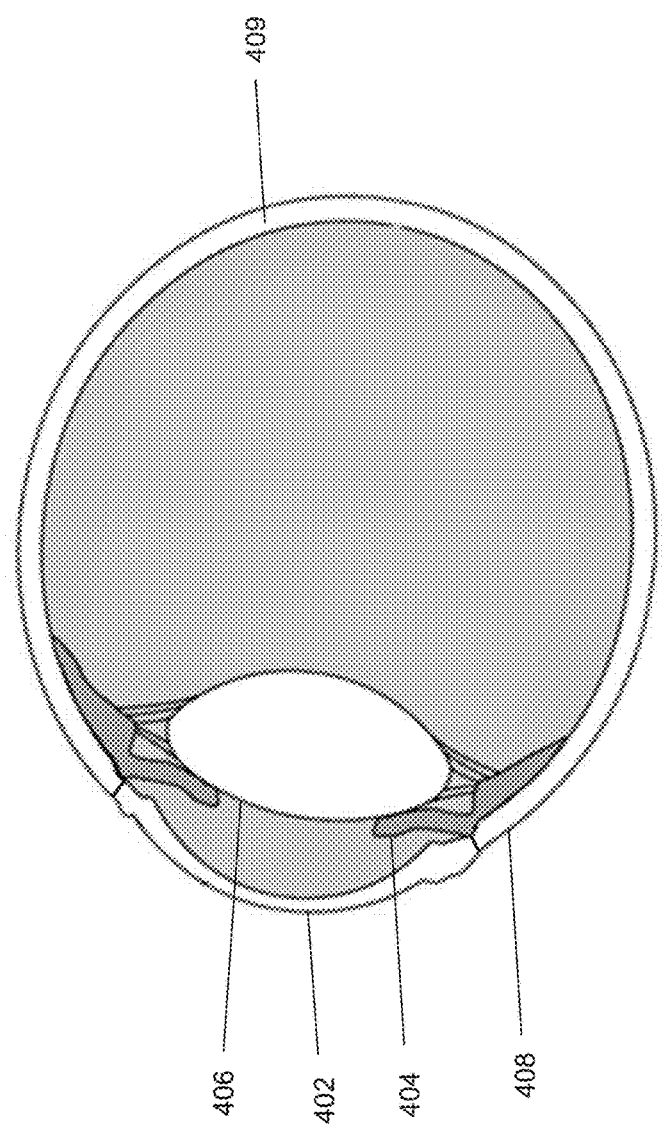
FIG. 1 is a schematic drawing of a portion of a human eye.
Figure 2A:
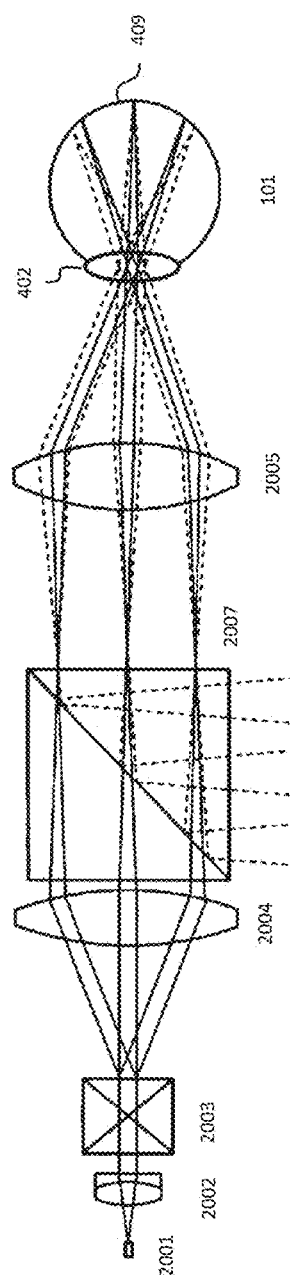
FIG. 2A illustrates an example of a known scanning module for an optical coherence tomography (OCT) system for scanning the retina of an eye.
Figure 2B:
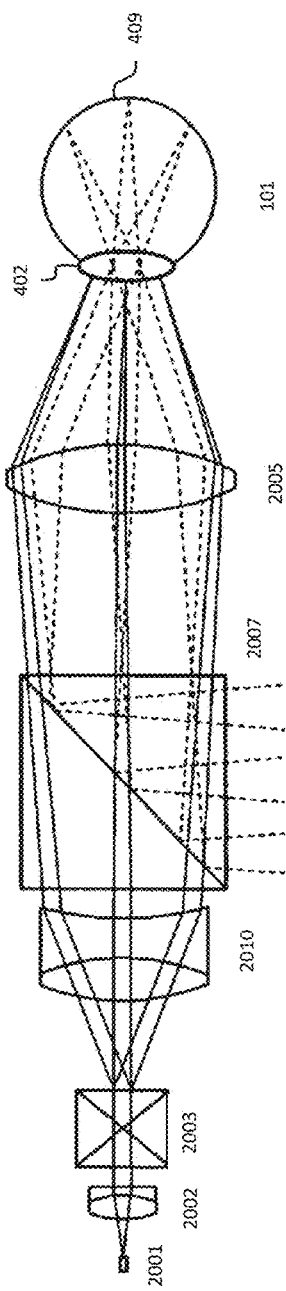
FIG. 2B illustrates an example of a known scanning module for an optical coherence tomography (OCT) system for scanning the cornea of an eye.

Exemplary embodiments of optical measurement systems and methods for measuring aberrations of an eye to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation. As used herein, "approximately" means with 30% (i.e., +/−30%) of a nominal value.

As described above, when planning a surgical procedure for implanting an intraocular lens, it is desired to obtain information about various characteristics of the eye, including both the cornea and the retina. Many of these characteristics can be obtained by an optical coherence tomography (OCT) system.

The present inventor has recognized that that for the purposes of planning an IOL surgery, sufficient information may be determined by scanning about a 9 mm diameter of the cornea and about a 3 mm diameter of the retina. Any pathology that would impact the surgery would be found in the central 9 mm diameter cornea scan. A scan diameter of 9 mm is enough that variations of corneal thickness that cause significant posterior corneal astigmatism can be measured and the amount of astigmatism ascertained. Such eyes are typically ones that have previously experienced a refractive procedure such as laser-assisted in situ keratomileusis (LASIK) or photorefractive keratectomy (PRK). Knowledge of the amount posterior astigmatism can be included in the planning for IOL surgery, including the selection of the best toric IOL.

On the retina, the decision that a premium IOL would be unsuitable can be determined if there are regions of unusually high reflectivity in the central 3 mm zone. Such reflective regions correspond to Drusen formation and they are indicative of retinal disease that will impact visual function.

Before surgery, with the lens with cataract is still in place, the primary factor resulting in poor vision is the cataract. After the removal of the cataract and implantation of an IOL, the poor retinal health would be the primary factor resulting in poor vision. The presence of Drusen also indicates that further degeneration of the retina is likely to continue, resulting in gradually worsening vision. Other conditions of concern such as a detached retinal layers may also be found.

A further advantage of having at least a 3 mm scan diameter on the retina is that it is possible to determine if the patient was staring straight into the instrument when the measurement is made. It is important that patient stare straight so the calculation of axial length is accurate. The foveal pit has a typical diameter of 0.7 mm. When a patient is fixated properly, the foveal pit will appear in the center of the retina scan image. If the patient is not fixated properly, the foveal pit will be found off center. However, as long as the foveal pit is found in the scan, an axial length may be calculated to it.

Toward this end, the present inventor has devised an OCT system, and a scanning module or subsystem for an OCT system, which may make optical coherence topography measurements of both the cornea and the retina of an eye. Beneficially, the solution which may permit simultaneous OCT scanning of the cornea and the retina of an eye. Also beneficially, embodiments of an OCT system, and a scanning module or subsystem for an OCT system, as described herein may operate without the use of a mechanized or motorized lens, and without manually moving a lens into and out of the optical path of the OCT probe beam.

An additional advantage of some embodiments disclosed below is that the scan diameter on lens 406 inside eye 101 is only slightly smaller than the diameter scanned on cornea 402. OCT data collected from lens 406 can be useful in planning IOL surgeries or in constructing a whole eye model of the anatomy of eye 101. However, just before reaching lens 406, the scan will also encounter iris 404 of eye 101. Accordingly, the OCT system may also reveal the structure of iris 404. The beam that reaches retina 409 is limited by iris 404. With a pivot point, as described below, in front of eye 101, a normal iris diameter of 6 mm will pass a beam that allows a 3 mm diameter scan on retina 409.

Figure 3A:
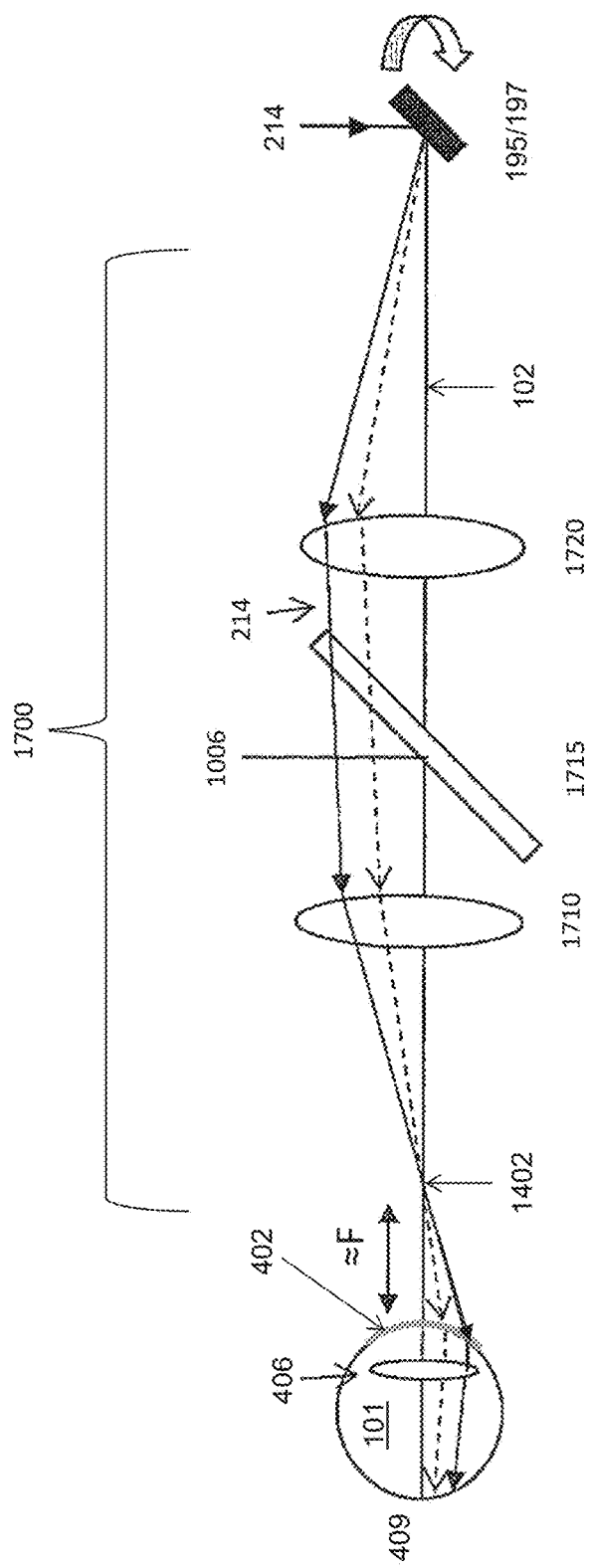
FIG. 3A illustrates an embodiment of a scanning module or subsystem of an OCT system for scanning the cornea and the retina of an eye.

FIG. 3A illustrates an embodiment of a scanning module or subsystem 3000 of an OCT system for scanning cornea 402 and retina 409 of eye 101.

Scanning module or subsystem 3000 includes a scanning mirror arrangement 195/197 and an optical system 1700.

Scanning mirror arrangement 195/197 includes at least one scanning mirror configured to receive an optical coherence topography (OCT) sample beam 214 and to scan the OCT sample beam 214 from a light output point of scanning mirror arrangement 195/197 at a plurality of different angles in both an x direction and in a y direction which is orthogonal to the x direction.

Optical system 1700 is configured to receive OCT sample beam 214 from the light output point of scanning mirror arrangement 195/197, and to provide OCT sample beam 214 to eye 101, including cornea 402 and retina 409.

Optical system 1700 includes a first lens 1710, a second lens 1720 and, optionally, a beamsplitter 1715.

First lens 1710 has a first focal length and is disposed along an optical axis 102 along an optical path from the light output point of scanning mirror arrangement 195/197 to eye 101 at a distance from cornea 402 which is approximately equal to the first focal length of first lens 1710.

Second lens 1720 is disposed along the optical path between first lens 1710 and the light output point of scanning mirror arrangement 195/197, and is arranged to receive OCT sample beam 214 from scanning mirror arrangement 195/197. Second lens 1720 is configured so as to provide OCT sample beam 214 to first lens 1710 as a converging beam, such that, for all of the plurality of different angles in which OCT sample beam 214 is scanned, OCT sample beam 214 passes through a pivot point 1402 located along optical axis 102 between cornea 402 and first lens 1710. Here, scan mirror arrangement 195/197 is arranged so that it is optically conjugate pivot point 1402 in front of cornea 402. In FIG. 3A, the solid rays correspond to a large angle of scanning mirror arrangement 195/197 with respect to optical axis 102, and the dashed rays correspond to a small angle of scanning mirror arrangement 195/197 with respect to optical axis 102.

Cornea 402 has a corneal focal length "F." Pivot point 1402 is located at a distance "F" from cornea 402. Here, a pivot point refers to a common point along optical axis 102 through which OCT sample beam 214 passes for all of the various angles which are scanned by scanning mirror arrangement 195/197 in the x direction and the y direction.

Figure 3B:
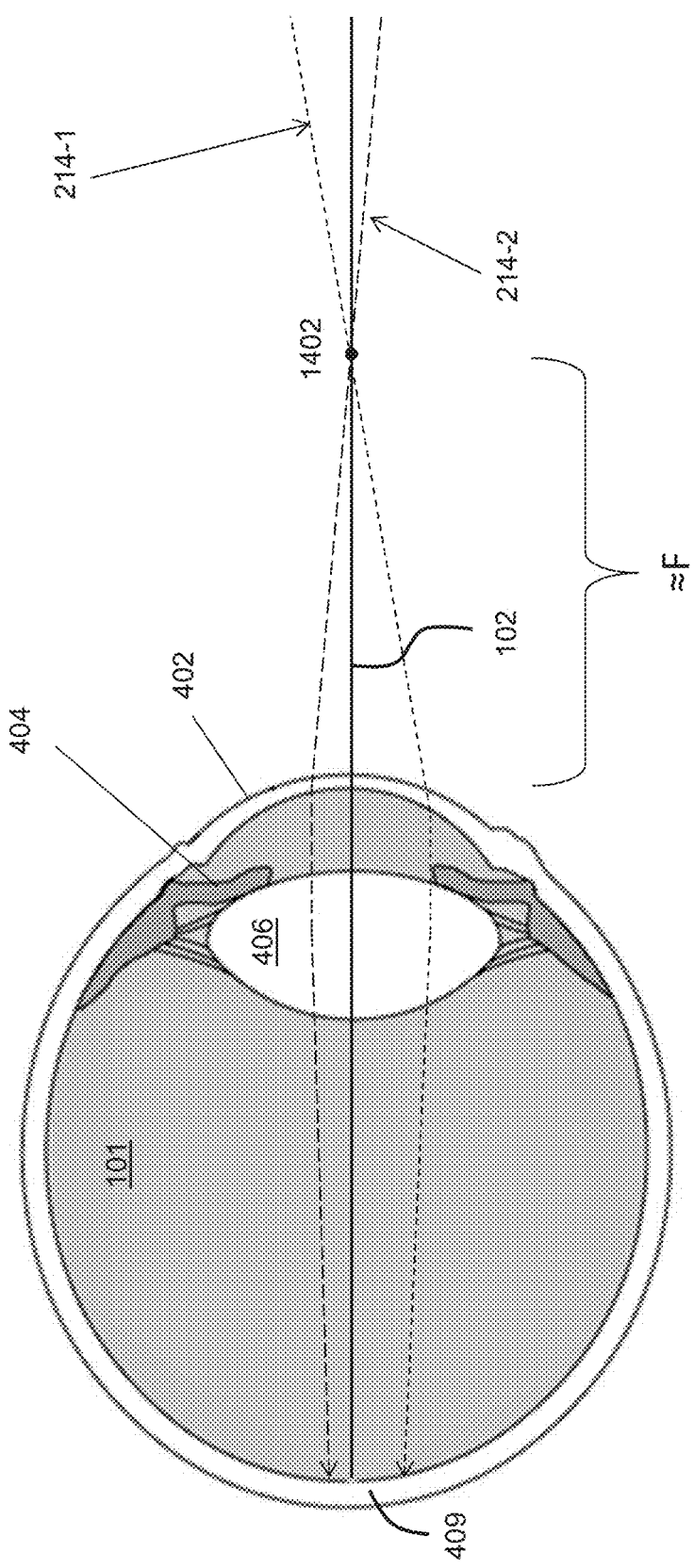
FIG. 3B illustrates in greater detail scan beams of the scanning module or subsystem of FIG. 3A of an OCT system for scanning the cornea and the retina of an eye.

FIG. 3B illustrates in greater detail example beams 214-1 and 214-2 which are created as OCT sample beam 214 is scanned across cornea 402 and retina 409 of eye 101. That is, beam 214-1 is one example of OCT sample beam 214 scanned at a first x angle in the x direction and a first y angle in the y direction at a first time, and beam 214-2 is another example of OCT sample beam 214 scanned a second x angle in the x direction and a second y angle in the y direction at a second time.

The optical power of a typical cornea 402 is 40 diopters which corresponds to a focal length of 25 mm. So, as best seen in FIG. 3B, if pivot point 1402 is located 25 mm in front of cornea 402, the scanned OCT sample beam 214 (e.g., beams 214=1 214-2) will be parallel to optical axis 102 in between cornea 402 and lens 406, for all x angles and y angles at which it is scanned. Beams 214-1 and 214-2 travel through iris 404, through the crystalline lens 406 and onto retina 409. Lens 409 bends off-axis light rays toward optical axis 102 so that OCT sample beam 214 executes a scan pattern on retina 409.

Beneficially, scanning module or subsystem 3000 may simultaneously scan a central region of cornea 402 and a large enough region of retina 409 that its health may be determined. Beneficially, scanning module or subsystem 3000 employs no motorized lens or auxiliary lens. Beneficially, scanning module or subsystem 3000 scans at least approximately a 9 mm diameter central region of cornea 402 and at least approximately a 3 mm diameter region of retina 409.

In a practical system there may be limitations on the diameter of first lens 1710. This tends to limit the range of angles that can be projected to pivot point 1402. So to meet clinical goals of corneal and retinal scan ranges, in some embodiments the ideal location of pivot point 1402 may be nearer or farther away from the 25 mm distance from cornea 402 of eye 101. For instance, the scan diameter of cornea 402 may be increased by moving pivot point 1402 further away from cornea 402 of eye 101, but at the expense of a reduced scan range on retina 409.

An advantage of scanning module or subsystem 3000 is that beam splitter 1715 may be placed, optionally, in an optical path in between first and second lenses 1710 and 1720. Light coupled onto optical axis 102 and/or returning light coupled off of optical axis 102 by beam splitter 1715 can couple light from other different optical paths 1006 into and/or out of eye 101 for other diagnostic or alignment purposes. Optical paths 1006 could be used for wavefront measurements, refraction measurements, iris imaging, pupil back illumination or topography measurements, such as corneal topography.

It should also be understood that the locations of: (1) second lens 1720 and scanning mirror arrangement 195/197; and (2) optical paths 1006 can be exchanged with respect to beam splitter 1715. That is, in some embodiments, second lens 1720 and scanning mirror arrangement 195/197 may be located "above" beam splitter 1715 in FIG. 3A and optical paths 1006 may be located to the right of beam splitter 1715 in FIG. 3A.

Typically the diameter of OCT sample beam 214 is small enough on both retina 409 and cornea 402 that sufficient transverse details are available simultaneously on both surfaces, and on crystalline lens 406, while OCT sample beam 214 is being scanned.

It is also possible to put optics in the OCT sample beam path so that the focus of the beam can be varied between focus on the cornea, lens or retina to obtain higher resolutions for specialized scans. For instance, the light for OCT sample beam 214 may be emitted from a single mode optical fiber and then passed through a lens that roughly collimates the beam. If the distance from the optical fiber to the lens is varied, a different amount of beam focus coming out of the lens can be created. That shift can move the beam waist in eye 101 from cornea 402 to retina 409, or other intermediate positions.

In some embodiments, the distance between first lens 1710 and pivot point 1402 is 60 mm, and the distance between first lens 1710 and cornea 402 is 85 mm. That places pivot point 1402 at a distance 25 mm in front of cornea 402 and, in general, creates a 9 mm scan diameter on cornea 402. This scan does not extend out into sclera 404 because a typical corneal diameter is 12 mm.

Accordingly, in some embodiments, after conducting the standard scan for cornea 402, an additional scan incorporating scleral region 404 may be desired. Applications where this may be desired include planning limbal relaxing incisions (LRI) or contact lens fitting. The increased scan diameter can be accomplished by moving first lens 1710 away from eye 101 an additional 15 mm so that pivot point 1402 is about 40 mm from cornea 402. Such a move may be accomplished automatically by a motorized stage that moves the entire instrument including first lens 1710, second lens 1720, etc. The increased distance of pivot point 1402 from eye 101 extends the scan into sclera 404. There may be a degradation in the resolution and accuracy of the data in the scleral region 404 compared to the data taken in cornea 402. However, in general, the reduced data quality is acceptable because procedures involving sclera 404 do not require as high a degree of accuracy as those involving cornea 402.

Figure 4A:
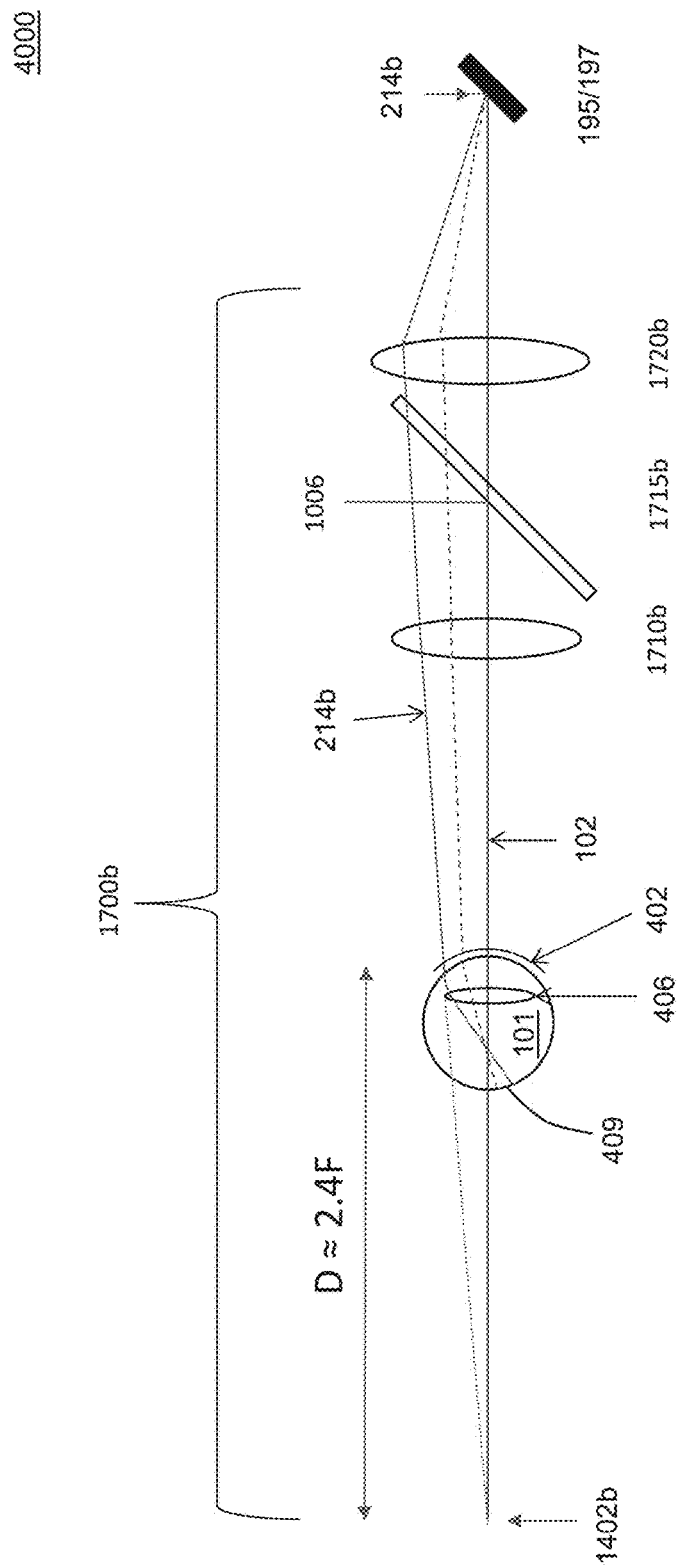
FIG. 4A illustrates another embodiment of a scanning module or subsystem of an OCT system for scanning the cornea and the retina of an eye.
Figure 4B:
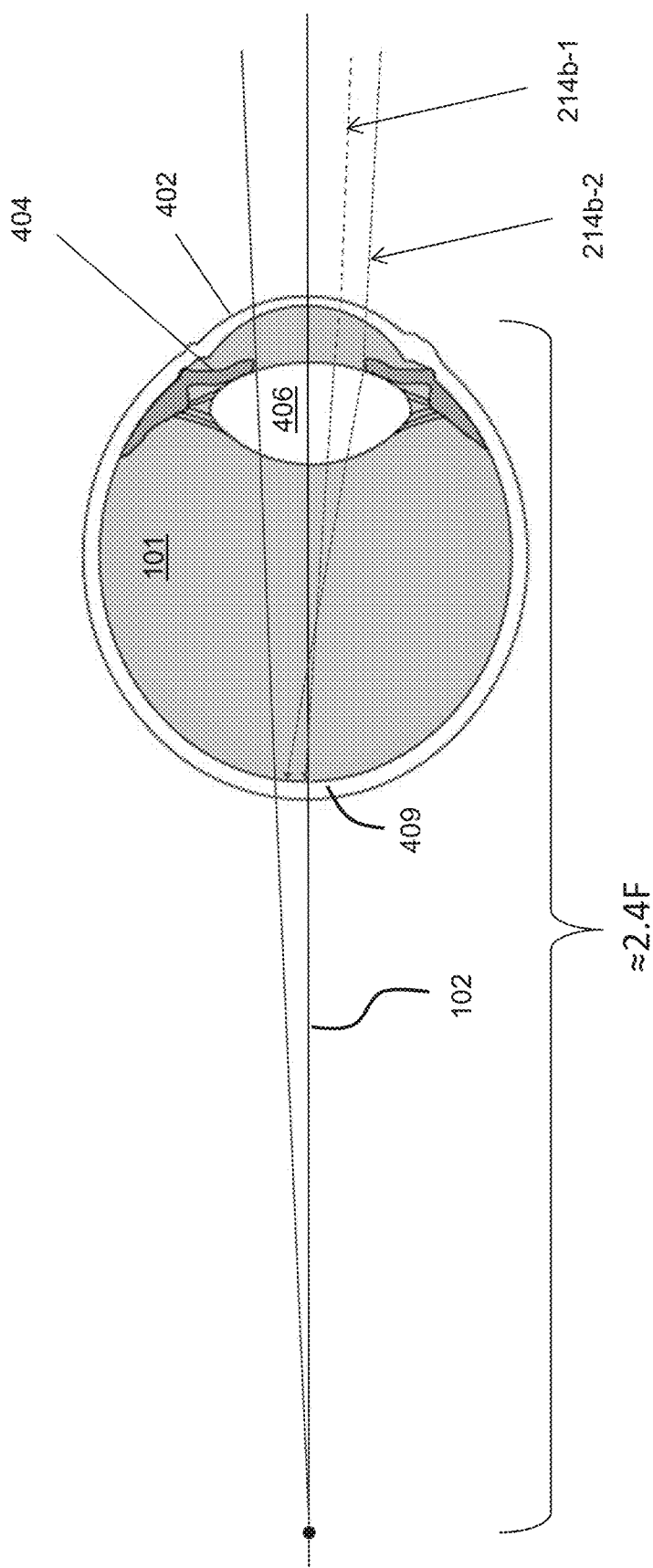
FIG. 4B illustrates in greater detail scan beams of the scanning module or subsystem of FIG. 4A of an OCT system for scanning the cornea and the retina of an eye.

FIG. 4A illustrates another embodiment of a scanning module or subsystem 4000 of an OCT system for scanning cornea 402 and retina 409 of eye 101.

Scanning module or subsystem 4000 includes scanning mirror arrangement 195/197 and an optical system 1700b.

Optical system 1700b is configured to receive OCT sample beam 214b from the light output point of scanning mirror arrangement 195/197, and to provide OCT sample beam 214b to eye 101, including cornea 402 and retina 409.

Optical system 1700b includes a first lens 1710b, a second lens 1720b and, optionally, a beamsplitter 1715b.

First lens 1710b is disposed along an optical axis 102 along an optical path from the light output point of scanning mirror arrangement 195/197 to eye 101. Beneficially, first lens 1710b has a first focal length and is disposed at a distance from cornea 402 which is approximately equal to the first focal length of first lens 1710b.

Second lens 1720b is disposed along the optical path between first lens 1710b and the light output point of scanning mirror arrangement 195/197, and is arranged to receive OCT sample beam 214b from scanning mirror arrangement 195/197. Second lens 1720b is configured so as to provide OCT sample beam 214b to first lens 1710b as a converging beam, such that, for all of the plurality of different angles in which OCT sample beam 214b is scanned, in the absence of eye 100 OCT sample beam 214b would intersect optical axis 102 at a pivot point 1402b located along optical axis 102 at a distance D behind cornea 402. Here, beneficially D is between 2 to 3 times the focal length of cornea 401, and most beneficially is approximately 2.4 times the focal length of cornea 402. For a typical eye 101, the focal length of cornea 402 is about 25 mm. In that case, D would be approximately 60 mm, such that pivot point 1402b is located approximately 60 mm behind cornea 402. In FIG. 4A, the solid line indicates a path that OCT sample beam 214b would follow to pivot point 1403b if eye 101 were not between scanning module or subsystem 4000 and eye 101, while the dashed green lines indicate scan beams passing through cornea 403, lens 406 and reaching retina 409.

FIG. B illustrates in greater detail example beams 214b-1 and 214b-2 which are created as OCT sample beam 214b is scanned across cornea 402 and retina 409 of eye 101. That is, beam 214b-1 is one example of OCT sample beam 214 scanned at a first x angle in the x direction and a first y angle in the y direction at a first time, and beam 214b-2 is another example of OCT sample beam 214b scanned a second x angle in the x direction and a second y angle in the y direction at a second time.

Beneficially, scanning module or subsystem 4000 may simultaneously scan a central region of cornea 402 and a large enough region of retina 409 that retinal health may be assessed. Beneficially, scanning module or subsystem 4000 employs no motorized lens or auxiliary lens. Beneficially, scanning module or subsystem 4000 scans at least approximately a 9 mm diameter central region of cornea 402 and at least approximately a 2.5 mm diameter region of retina 409.

Compared to scanning module or subsystem 3000 with optical system 1700 and pivot point 1402 in front of eye 101, in some embodiments scanning module or subsystem 4000 with optical system 1700b and pivot point 1402b beyond or behind eye 101 gives about 15% less scan diameter on lens 406 and about 30% less scan on retina 409 when the same corneal scan diameters are considered. Of course changes in optics in the OCT system can increase the diameter scanned on cornea 403, but the retinal scan diameter with scanning module or subsystem 4000 having pivot point 1403b beyond or behind eye 101 is smaller than with pivot point 1402 in front of eye 101 because the scan rays are more converging as they pass through iris 404. Also, with pivot point 1402b beyond or behind eye 101, the diameter required for first lens 1710b sending light to eye 101 needs to be about 40% larger in diameter than first lens 1710 with pivot point 1402 in front of eye 101. This larger lens diameter is disadvantageous if the OCT system is being built into a multi-purpose system, such as a system described below with respect to FIGS. 5, 7, 8A and 8B, which also includes a corneal topographer because central cornea measurements require lights placed near to the optical axis of the instrument. Despite these several disadvantages, an OCT scanning system with pivot point 1402b placed beyond or behind eye 101 still results in an effective system for simultaneous scans of cornea 402, lens 406 and retina 409. A potential advantage of a system using pivot point 1402b placed beyond or behind eye 101 is that focal lengths of lenses 1710b and 1720b used to create such a system may be a bit longer and simpler in construction when designing for a given level of low optical aberrations.

Figure 5:
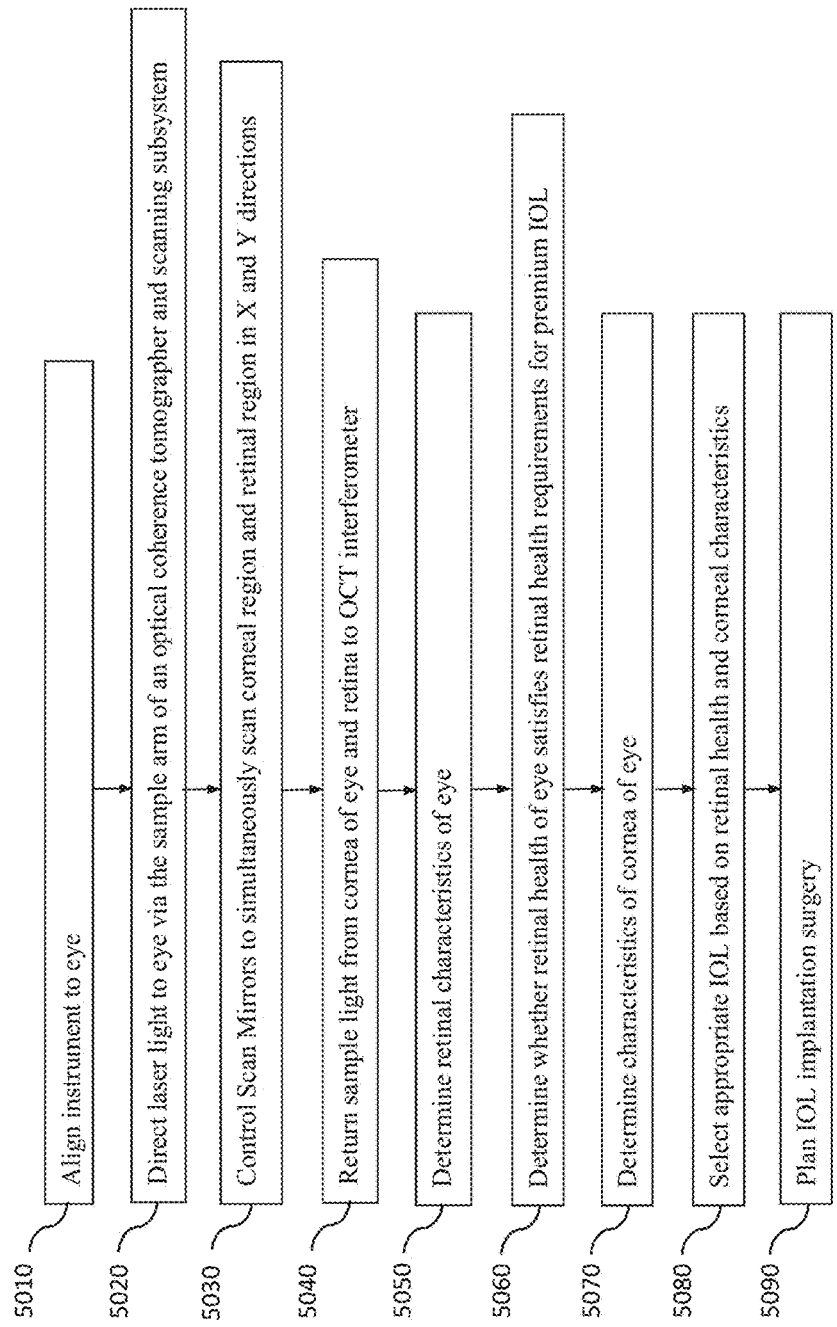
FIG. 5 is a flowchart of an example embodiment of a method of measuring an optical characteristic of an eye.

FIG. 5 is a flowchart of an example embodiment of a method 5000 of measuring one or more characteristics of an eye with an eye measurement instrument, using an OCT scanning module or subsystem such as the OCT scanning module or subsystem 3000.

An operation 5010 includes aligning the eye measurement instrument to the eye under examination.

An operation 5020 includes directing a sample light beam to the eye via the sample arm of an optical coherence tomographer (OCT) system and via an OCT scanning subsystem which includes a scanning mirror arrangement and an optical system.

An operation 5030 includes controlling the scanning mirror arrangement to scan the light beam simultaneously across a corneal region of the eye and a retinal region of the eye. Beneficially, the corneal region has a diameter of at least approximately 9 millimeters and the retinal region has a diameter of at least approximately 3 millimeters.

An operation 5040 includes returning the sample light from the cornea of the eye and the retina of the eye to an OCT interferometer of the OCT system.

An operation 5050 includes determining at least one retinal characteristic of the eye from the returned sample light from the retina of the eye. For example, operation 5050 may include determining whether or not whether the retinal region includes any areas having a reflectivity which us greater than a specified threshold.

An operation 5060 includes determining from the at least one retinal characteristic of the eye whether the retinal health of the eye satisfies one or more retinal health requirements. In some embodiments, this may include determining whether the retinal region includes Drusen formation.

An operation 5070 includes determining at least one corneal characteristic of the eye from the returned sample light from the cornea of the eye.

An operation 5080 includes selecting an IOL for implantation into the eye based on the at least one corneal characteristic and whether the retinal health of the eye satisfies one or more retinal health requirements.

An operation 5090 includes planning an IOL implantation surgery, wherein the planning includes using at least the selected IOL. The planning may be made using one or more characteristics of the eye obtained via the OCT scan of the eye and/or wavefront measurements of the eye and/or a corneal topography of the eye. Such characteristics may include the corneal thickness, anterior corneal radius, posterior corneal radius, anterior chamber depth, anterior lens radius, lens thickness, posterior lens radius, and/or total eye length.

The principles of an OCT system including OCT scanning subsystem 3000 as described above, may be applied to an optical measurement instrument which includes additional functionality, such as the ability to measure corneal topography and/or to make wavefront aberrometry measurements for they eye. Embodiments of such an optical measurement instrument, and methods of operation thereof, will now be described.

Figure 6C:
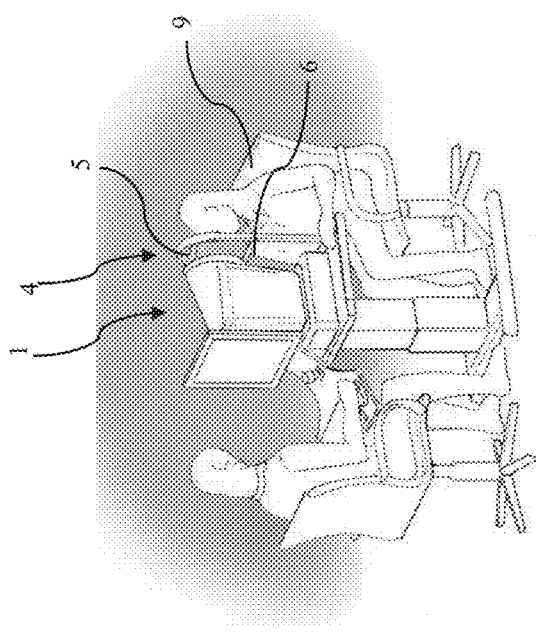
FIG. 6C illustrates a side perspective view showing an optical measurement system according to many embodiments.
Figure 6A:
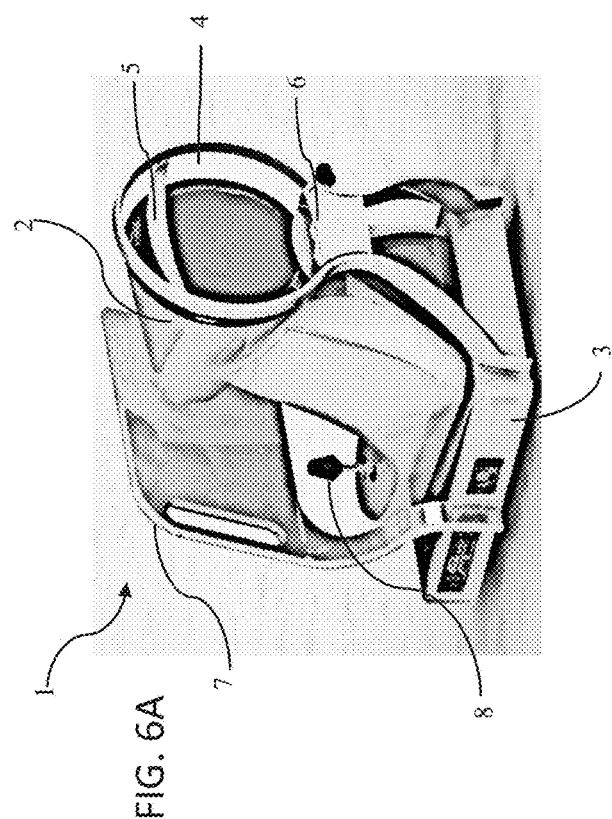
FIG. 6A illustrates a front perspective view showing an optical measurement system according to many embodiments.
Figure 6B:
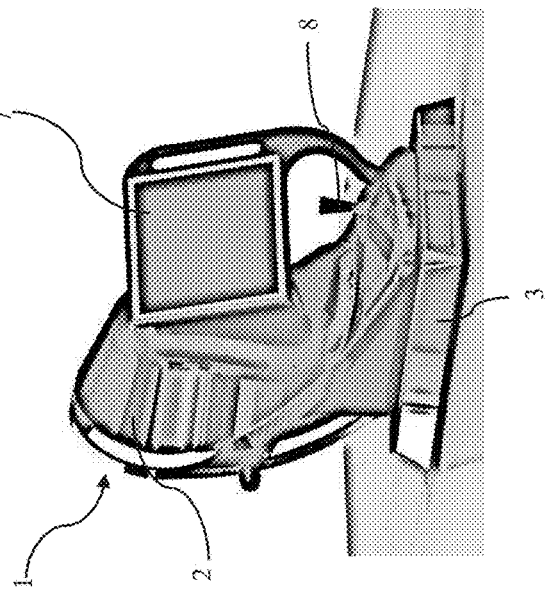
FIG. 6B illustrates a rear perspective view showing an optical measurement system according to many embodiments.

As shown in FIGS. 6A-6C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system 1includes a main unit 2 which comprises a base 3 and includes many primary subsystems of many embodiments of optical measurement system 1. For example, externally visible subsystems include a touch-screen display control panel 7, a patient interface 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by optical measurement system 1.

In one embodiment patient interface 4 includes a chin support 6 and/or a forehead rest 5 configured to hold the head of the patient in a single, uniform position suitably aligned with respect to optical measurement system 1 throughout the diagnostic measurement. As shown in FIG. 6C, the optical measurement system 1 may be disposed so that the patient may be seated in a patient chair 9. Patient chair 9 can be configured to be adjusted and oriented in three axes (x, y, and z) so that the patent's head can be at a suitable height and lateral position for placement on the patient interface.

In many embodiments, optical measurement system 1 may include external communication connections. For example, optical measurement system 1 can include a network connection (e.g., an RJ45 network connection or WiFi) for connecting optical measurement system 1 to a network. The network connection can be used to enable network printing of diagnostic reports, remote access to view patient diagnostic reports, and remote access to perform system diagnostics. Optical measurement system 1 can include a video output port (e.g., HDMI) that can be used to output video of diagnostic measurements performed by optical measurement system 1. The output video can be displayed on an external monitor for, for example, viewing by physicians or users. The output video can also be recorded for, for example, archival or training purposes. Optical measurement system 1 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery. Other uses of network data include obtaining service logs, outcomes analysis and algorithm improvement.

Figure 7:
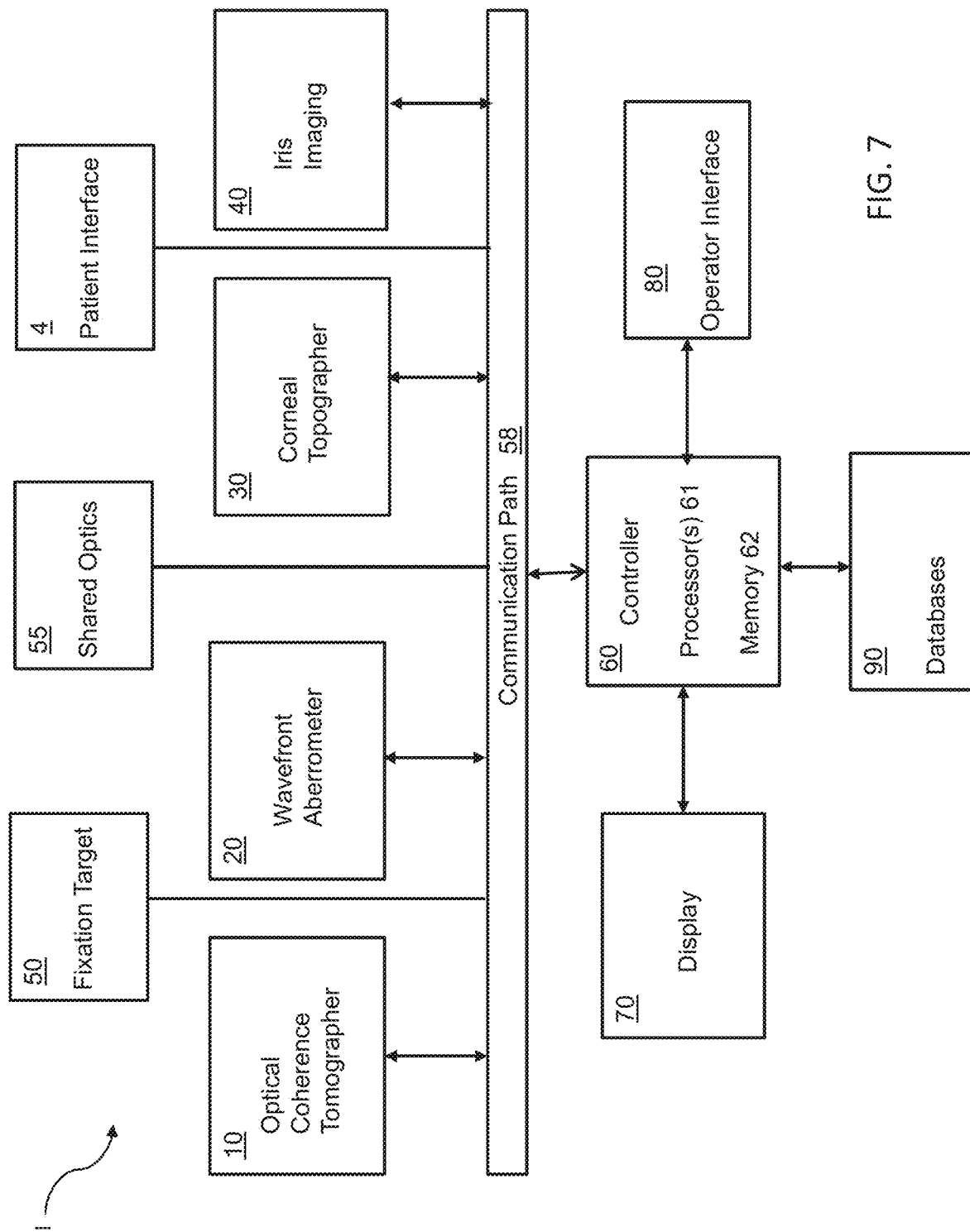
FIG. 7 is a block diagram of a system including an optical measurement instrument, and a position of an eye relative to the system according to one or more embodiments described herein which may be used by the optical measurement.

FIG. 7 is a block diagram of optical measurement system 1 according to one or more embodiments described herein. Optical measurement system 1 includes: an optical coherence tomography (OCT) subsystem 10, a wavefront aberrometer subsystem 20, and a corneal topographer subsystem 30 for measuring one or more characteristics of a subject's eye. Optical measurement system 1 may further include an iris imaging subsystem 40, a fixation target subsystem 50, a controller 60, including one or more processor(s) 61 and memory 62, a display 70 and an operator interface 80.

Optical measurement system 1 further includes patient interface 4 for a subject to present his or her eye 101 for measurement by optical measurement system 1.

As noted above, optical coherence tomography subsystem 10 may be configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by controller 60 for a number of purposes, including, in some embodiment to program and control a subsequent laser-assisted surgical procedure. The spatial disposition of the structures of interest and/or of suitable matching geometric modeling can also be used to determine a wide variety of parameters. Beneficially, optical coherence tomography subsystem 10 may employ swept source optical coherence tomography (SS-OCT) or spectral domain OCT (SDOCT). In some embodiments, OCT subsystem 10 may include OCT scanning subsystem 3000.

Wavefront aberrometer subsystem 20 is configured to measure ocular aberrations, which may include low and high order aberrations, by measuring the wavefront emerging from the eye by, for example a Shack-Hartman wavefront sensor.

Corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target subsystem 50 is configured to control the patient's accommodation and alignment direction, because it is often desired to measure the refraction and wavefront aberrations when an eye under measurement is focused at its far point Images captured by corneal topographer subsystem 10, wavefront aberrometer 20, optical coherence tomographer subsystem 30 or camera 40 may be displayed with a display of operator interface 80 or display 70 of optical measurement system 1, respectively. Operator interface 80 may also be used to modify, distort, or transform any of the displayed images.

Shared optics 55 provide a common propagation path that is disposed between patient interface 4 and each of optical coherence tomography (OCT) subsystem 10, wavefront aberrometer subsystem 20, corneal topographer subsystem 30, and in some embodiments, camera 40, and fixation target subsystem 50. In many embodiments, shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

Controller 60 controls the operation of optical measurement system 1 and can receive input from any of optical coherence tomographer (OCT) subsystem 10, wavefront aberrometer subsystem 20, corneal topographer subsystem 30 for measuring one or more characteristics of a subject's eye, camera 40, fixation target subsystem 50, display 70 and operator interface 80 via communication paths 58. Controller 60 can include any suitable components, such as one or more processor, one or more field-programmable gate array (FPGA), and one or more memory storage devices. In many embodiments, controller 60 controls display 70 to provide for user control over the laser eye surgery procedure for pre-cataract procedure planning according to user specified treatment parameters as well as to provide user control over the laser eye surgery procedure. Communication paths 58 can be implemented in any suitable configuration, including any suitable shared or dedicated communication paths between controller 60 and the respective system components.

Operator interface 80 can include any suitable user input device suitable to provide user input to controller 60. For example, user interface devices 80 can include devices such as joystick 8, a keyboard, or a touchscreen display.

Figure 8A:
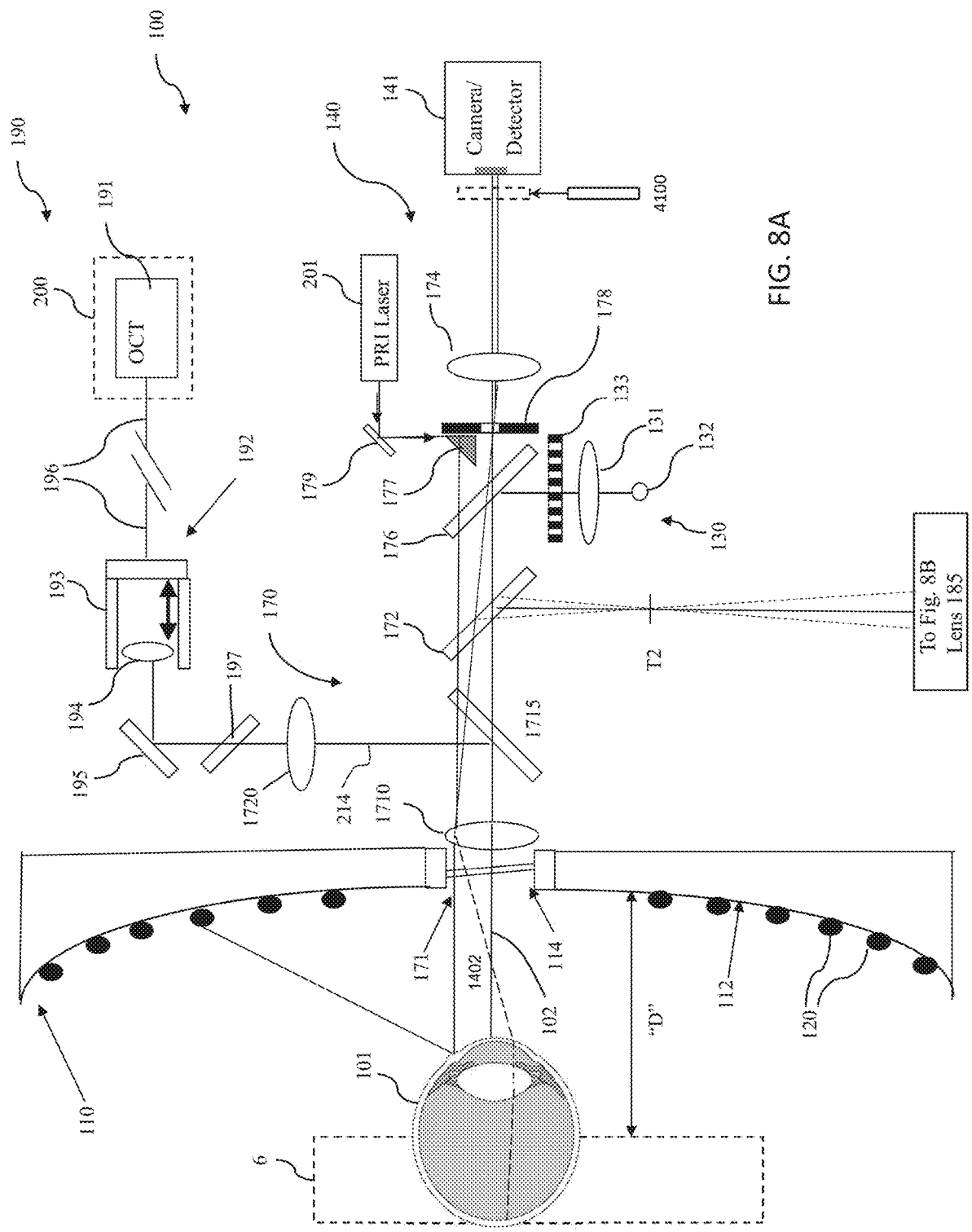
FIGS. 8A and 8B illustrate together an assembly illustrating a suitable configuration and integration of an optical coherence tomographer subsystem, a wavefront aberrometer subsystem, a corneal topographer subsystem, an iris imaging subsystem, a fixation target subsystem according to a non-limiting embodiment of the present invention.
Figure 8B:
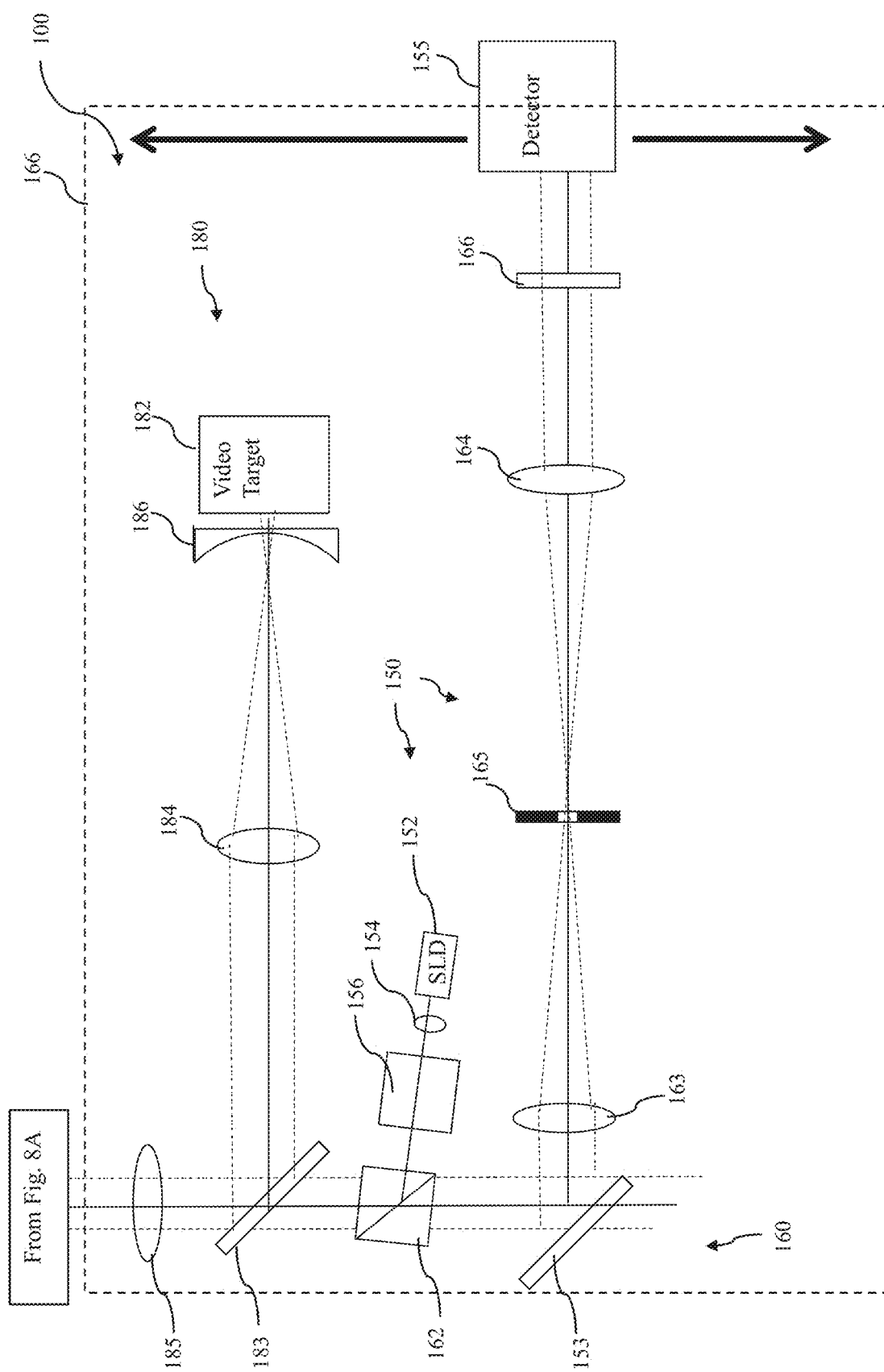

FIGS. 8A and 8B are simplified block diagrams illustrating an assembly 100 according to many embodiments which may be included in optical measurement system 1. Assembly 100 is a non-limiting example of suitable configurations and integration of an optical coherence tomography (OCT) subsystem 190, a wavefront aberrometer subsystem 150, a corneal topographer subsystem 140 for measuring one or more characteristics of a subject's eye 101, camera 40, a fixation target subsystem 180 and shared optics.

The shared optics generally comprise one or more components of a first optical system 170 disposed along a central axis 102 passing through the opening or aperture 114 of the structure 110. First optical system 170 directs light from the various light sources along the central axis 102 towards an eye 101 and establishes a shared or common optical path along which the light from the various light sources travel to eye 101. In one embodiment, optical system 170 comprises a quarter wave plate 171, a first beamsplitter 172, a second beamsplitter 1715, an optical element (e.g., a lens) 174, a lens 1710, a third beamsplitter 176, and a structure including an aperture 178. Additional optical systems may be used in assembly 100 to direct light beams from one or more light sources to the first optical system 170. For example, a second optical system 160 directs light to the first optical system 170 from wavefront aberrometer subsystem 150 and comprises mirror 153, beam splitter 183 and lens 185.

Other configurations of assembly 100 may be possible and may be apparent to a person of skill in the art.

Corneal topographer subsystem 140 comprises a structure 110 having a principal surface 112 with an opening or aperture 114 therein; a plurality of first (or peripheral) light sources 120 provided on the principal surface 112 of structure 110; a Helmholz light source 130; and a detector, photodetector, or detector array 141, for example a camera.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 101, as illustrated in FIG. 8A.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 1001 without being obstructed by the subject's nose. Of course, a variety of other configurations and shapes for principal surface 112 are possible.

In the embodiment of FIG. 8A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 8A).

In operation, a ray (solid line) from one of the first light sources 120 is reflected by the cornea and passes through optical system 170, to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 101 and/or the shape of the cornea. Thus, detector array 141 detects the light spots projected thereon and provides corresponding output signals to a processor of controller 60 (FIG. 7). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 60 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, lamps of second light sources 132 are located off the central optical axis 102 of assembly 100, and light from second light sources 132 is directed toward optical element 171 by third beamsplitter 176.

The operation of the topographer portion of assembly 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 141 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by assembly 100 without a "hole" or missing data from the central corneal region.

As seen in FIG. 8A, assembly 100 also includes movable optical element 4100 which may be selectively moved into and out of an optical path between eye 101 and detector array 141 along optical axis 102. Although not shown in FIGS. 8A and 8B, assembly 100 may further include light sources 3200 as described above with respect to FIGS. 3A and 3B.

In some embodiments, contemporaneous with obtaining the eye measurement data (e.g., wavefront aberrometry data and/or corneal topographer data) for eye 101, an image of sclera 408 of eye 101 may be captured by detector array 141. The image may be processed by a processor (e.g., processor 61 of controller 60) executing a pattern recognition algorithm as known in the art to identify unique features of sclera 408, for example blood vessels. Processor 61 may execute a pattern recognition algorithm as a set of computer instructions stored in a memory (e.g., memory 62) associated with processor 61. Processor 61 may use the identified features from the image of eye 101 as fiducials or registration markers for the eye measurement data for eye 101. In some embodiments, processor 61 may store in memory 62 the eye measurement data (e.g., wavefront aberrometry data and/or corneal topographer data), a first image of eye 101 focused at the appropriate image plane for the eye measurement data (e.g., focused at iris 404 for wavefront measurement data), a second image of eye 101 focused at the fiducials (e.g., scleral blood vessels 410), and registration data which registers the eye measurement data to the locations of the identified features or fiducials in the image of eye 101. This set of data may be used by a surgical instrument in a subsequent surgery. For example, the surgical instrument may include a camera which is able to capture an image of eye 101, including the fiducials. By mapping the fiducials identified by assembly 100 to the same fiducials observed by the camera of the surgical instrument, the eye measurement data may be registered to the locations of the fiducials observed by the camera of the surgical instrument via the registration data of assembly 100.

A fourth light source 201 off the central axis 102 may be directed along optical axis 102 by mirrors 177, 179 disposed on or near the aperture 178, perpendicular to the optical axis 102 are configured as a pupil retroreflection illuminator. The pupil retroreflecton illuminator is configured to direct a disc of light toward patient's eye 101, whereby the disc of light may be reflected from reflective surfaces within eye 101, and the reflected light is transmitted by optical path 170 to detector 141. The pupil retroreflection illuminators may optionally be configured such that, when the patient's pupil is dilated, the disc of light from light source 201 is reflected from an implanted IOL to image the IOL, including any fiducial marks; if IOL is imperfectly placed, detector 141 may be used to determine IOL edges are decentered. Also, images from detector 141 using the pupil retroreflection illuminator may see folds, for instance, unfolded edge if the IOL did not unfold properly.

Wavefront aberrometer subsystem 150 of assembly 100 comprises a third light source 152 providing a probe beam and a wavefront sensor 155. Wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows assembly 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 100, and at least a portion of the scattered light passes back through aperture 114 to first beamsplitter 172. First beamsplitter 172 directs the back scattered light back through beam splitter 172 to polarizing beamsplitter 162, mirror 153 to wavefront sensor 155.

Wavefront sensor 155 outputs signals to a processor of controller 60 which uses the signals to determine ocular aberrations of eye 101. Preferably, the processor is able to better characterize eye 101 by considering the corneal topography of eye 101 measured by corneal topography subsystem 140, which may also be determined by the processor based on outputs of detector array 141, as explained above.

In operation of wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then the light travels through the cornea and focuses onto the retina of eye 101.

The focused spot of light becomes a light source that is used to characterize eye 101 with wavefront sensor 155. Light from the probe beam that impinges on the retina of eye 101 scatters in various directions. Some of the light reflects back as a semi-collimated beam back towards assembly 100. Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 so as to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to a processor of controller 60 and analyzed to compute the refraction and aberrations of eye 101.

OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source of OCT assembly 191, a Z-scan device 193 operable to alter the focus of the beam in the Z-direction (i.e., along the direction of propagation of the OCT beam) under control of the controller, and X-scan device 195, and a Y-scan device 197 operable to translate the OCT beam in the X and Y directions (i.e., perpendicular to the direction of propagation of the of the OCT beam), respectively, under control of controller 60. The OCT light source and reference arm may be incorporated into assembly 100 of optical measurement system 1 shown in FIG. 8A. Alternatively, OCT assembly 191 may be housed in a second unit or housing 200 and the OCT beam from the OCT source may be directed from second unit 200 to the main unit by optical pathway 192.

Beneficially, the OCT systems and methods employed in optical measurement system 1 and assembly 100 may employ swept source optical coherence tomography (SS-OCT) as described above. Beneficially, optical measurement system 1, assembly 100 and OCT subsystem 190 may each comprise OCT interferometer 1000, 3000 or 4000.

As explained above, in SS-OCT, a rapid-scanning laser source is employed. By rapidly sweeping the source wavelength over a broad wavelength range, and collecting all the scattering and reflection information at each wavelength and at each position, the collected spectral data may be inverse-Fourier-transformed to recover the spatial depth-dependent information for the object under test (e.g., eye 101).

In operation, as shown in FIG. 8A, after exiting connector 212, OCT probe beam 214 may be collimated, for example using a collimating optical fiber 196. Following collimating fiber 196 OCT probe beam 214 is optionally directed to Z-scan device 193 operable to change the focal point of OCT probe beam 214 in the Z-direction, and X- and Y-scan devices 195 and 197, which are operable to scan the OCT beam in X and Y-directions perpendicular to the Z-direction.

Following the collimating optical fiber 196, OCT probe beam 214 continues through a Z-scan device 193. Z-scan device 193 may comprise a Z-telescope 194 which is operable to scan focus position of OCT probe beam 214 in the patient's eye 101 along the Z axis. For example, Z-telescope 194 may include a Galilean telescope with two lens groups (each lens group includes one or more lenses). One of the lens groups moves along the Z axis about the collimation position of Z-scan device 193. In this way, the focus position in the patient's eye 101 moves along the Z axis. In general, there is a relationship between the motion of lens group and the motion of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. Z-telescope 194 functions as a Z-scan device for changing the focus point of OCT probe beam 214 in patient's eye 101. Z-scan telescope 194 can be controlled automatically and dynamically by controller 60 and selected to be independent or to interplay with X and Y scan devices 195 and 197.

After passing through the z-scan device, the OCT probe beam 214 is incident upon an X-scan device 195, which is operable to scan the OCT probe beam 214 in the X direction, which is dominantly transverse to the Z axis and transverse to the direction of propagation of OCT probe beam 214. X-scan device 195 is controlled by controller 60, and can include suitable components, such as a lens coupled to a MEMS device, a motor, galvanometer, or any other well-known optic moving device. The relationship of the motion of OCT probe beam 214 as a function of the motion of the actuator of X-scan device 195 does not have to be fixed or linear. Modeling or calibrated measurement of the relationship or a combination of both can be determined and used to direct the location of OCT probe beam 214.

After being directed by the X-scan device 195, OCT probe beam 214 is incident upon a Y scan device 197, which is operable to scan OCT probe beam 214 in the Y direction, which is dominantly transverse to the X and Z axes. Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator of Y-scan device 197 does not have to be fixed or linear. Modeling or calibrated measurement of the relationship or a combination of both can be determined and used to direct the location of OCT probe beam 214. Alternatively, the functionality of X-Scan device 195 and Y-Scan device 197 can be provided by an XY-scan device configured to scan OCT probe beam 214 in two dimensions transverse to the Z axis and the propagation direction of OCT probe beam 214. The X-scan and Y scan devices 195, 197 change the resulting direction of OCT probe beam 214, causing lateral displacements of OCT probe beam 214 located in the patient's eye 101.

OCT probe beam 214 is then directed to beam splitter 1715 through lens 1720, and thence through lens 1710, quarter wave plate 171 and aperture 114 and to the patient eye 101. Reflections and scattering off of structures within the eye provide return beams that retrace back through the patient interface quarter wave plate 171, lens 1710, beam splitter 1715, lens 1720, Y-scan device 197, X-scan device 195, Z-scan device 193, optical fiber 196 and beam combiner 204 (FIG. 6), and back into the OCT detection device. The returning back reflections of the sample arm are combined with the returning reference portion and directed into the detector portion of the OCT detection device, which generates OCT signals in response to the combined returning beams. The generated OCT signals that are in turn interpreted by controller 60 to determine the spatial disposition of the structures of interest in patient's eye 101. The generated OCT signals can also be interpreted by the controller to determine the spatial disposition of the structures of interest in the patient's eye 101. The generated OCT signals can also be interpreted by the control electronics to align the position and orientation of the patient eye 101 within patient interface 4.

Optical measurement systems disclosed herein may comprise an iris imaging subsystem 40. Iris imaging subsystem 40 generally may comprise an infrared light source, for example an infrared light source 152, and detector 141. In operation light from light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in X, Y and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 101. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of optical measurement system 1 by methods described, for instance, in "Method for registering multiple data sets," U.S. Patent Appl. No. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, patient movement between measurements (and/or during a measurement sequence) can be identified, as well as changes in the eye itself (including those induced by the measurement, such as changes in the size of the pupil, changes in pupil location, etc.).

In many embodiments, optical measurement system 1 includes fixation target subsystem 50 (FIG. 7), and accordingly assembly 100 shown in FIGS. 8A and 8B includes fixation target subsystem 180 which includes a fixation target 182 for the patient to view. Fixation target subsystem 180 is used to control the patient's accommodation and alignment, because it is often desired to measure the refraction and wavefront aberrations when eye 101 is focused at its far point (e.g., because LASIK treatments are primarily based on this). In fixation target subsystem 180, a projection of a target, for instance a cross-hair pattern is projected onto eye 101 of the patient, the cross hair pattern being formed, e.g. by fixation target 182 comprising a backlit LED and a film.

In operation, light originates from fixation target 182 and lenses 186 and 184. Lens 185 collects the light and forms an aerial image T2. This aerial image T2 is the one that the patient views. The patient focus is maintained on aerial image T2 during measurement so as to maintain the eye in a fixed focal position. In some embodiments, fixation target 182 may comprise a video target which may have a variable center location under control of one or more processors 61 of controller 60, for example a blinking dot which may cause aerial image T2 to appear at a plurality of different angular locations (e.g., five different angular locations) relative to eye 101. In this case, the patient may be instructed to gaze at the blinking dot as it moves from location to location to create a plurality of different gaze angles for eye 101. Accordingly, optical coherence tomography subsystem 10 may collect OCT data sets for retina 409 for each of the plurality of gaze angles, e.g., five different gaze angles, causing five different regions of retina 409 to be sampled. In that way, in some embodiments the total combined scanned diameter retina 409 could be expanded from 3 mm to a larger region with a diameter of approximately 6 mm, providing a larger area of retina 409 from which retinal health may be evaluated.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan measures at least the locations of the retina, the cornea and one of anterior portion of the patient's lens. An iris image may be taken simultaneously with or sequentially with each of the measurements taken with wavefront aberrometry subsystem, the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Optical measurement system 1 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of preoperative measurements obtained from the optical measurement system 1, a contemplated surgical intervention, and on or more algorithms or models stored in the memory of the optical measurement system 1 and executed by the processor. The contemplated surgical intervention may include the selection of an IOL for placement, the alignment of a toric IOL in the eye, the selection of an IOL characteristic, the nature or type of incision to be used during surgery (e.g., relaxation incision), or one or more post-operative vision characteristics requested by the patient.

Optical measurement system 1 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement system 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

Optical measurement system 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

Optical measurement system 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement system 1, in conjunction with measurement data of a subject's eye obtained by optical measurement system 1, for cataract diagnostics or cataract treatment planning, which may include specifying and/or selecting a particular IOL for a subject's eye. For example, one or more processors of optical measurement system 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement system 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, may comprise: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, may comprise: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device may store computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position may comprise: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, may comprise: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

An improved method for planning a refractive treatment of an eye of a patient may comprise: measuring a plurality of ocular biometry information, anterior corneal surface information, posterior corneal surface information, anterior lens surface information, and posterior lens surface information, lens tilt information and lens position information.

A method of customizing at least one parameter of an intraocular lens, may comprise: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a post-operative condition of the eye based at least partially on the measured eye characteristics; and predictively estimating, in accordance with an output of said empirically calculating and the eye characteristics, with at least one parameter of the intraocular lens to obtain the desired postoperative condition.

A method of adjusting the refractive power in an eye of a patient who has undergone cataract surgery may comprise: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure ; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g.,"such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

I claim:

1. A method, comprising:
   aligning an eye measurement instrument to an eye;
   directing a sample light beam to the eye via a sample arm of an optical coherence tomographer (OCT) system and via an OCT scanning subsystem which includes a scanning mirror arrangement and an optical system;
   controlling the scanning mirror arrangement to scan the light beam simultaneously at a plurality of different angles across a corneal region of the eye and a retinal region of the eye, wherein the corneal region has a diameter of at least approximately 9 millimeters and the retinal region has a diameter of at least approximately 2.5 millimeters;
   returning the sample light from the cornea of the eye and the retina of the eye to an OCT interferometer of the OCT system;
   determining at least one retinal characteristic of the eye from the returned sample light from the retina of the eye;
   determining from the at least one retinal characteristic of the eye whether a retinal health of the eye satisfies one or more retinal health requirements for implanting a premium intraocular lens into the eye;
   determining at least one corneal characteristic of the eye from the returned sample light from the cornea of the eye;
   selecting an IOL for implantation into the eye based on the at least one corneal characteristic and whether the retinal health of the eye satisfies one or more retinal health requirements; and
   planning an IOL implantation surgery, wherein the planning includes using at least the selected IOL.

2. The method of claim 1, further comprising performing the planned IOL implantation surgery using selected IOL.

3. The method of claim 1, wherein the at least one corneal characteristic includes a thickness of the cornea.

4. The method of claim 3, wherein the planning includes using the corneal thickness.

5. The method of claim 1, wherein the at least one retinal characteristic includes whether the retinal region includes any areas having a reflectivity which us greater than a specified threshold.

6. The method of claim 5, wherein determining from the at least one retinal characteristic of the eye whether a retinal health of the eye satisfies one or more retinal health requirements includes determining whether the retinal region includes Drusen formation.

7. The method of claim 1, wherein the optical system includes:
   a first lens having a first focal length, the first lens being disposed along an optical axis along an optical path from a light output point of the scanning mirror arrangement to the eye at a distance from the cornea which is approximately equal to the first focal length, and a second lens disposed along the optical path between the first lens and the light output point of the scanning mirror arrangement, the second lens being arranged to receive the sample beam from the scanning mirror arrangement and provide the sample beam to the first lens as a converging beam such that, for all of the plurality of different angles, the sample beam passes through a pivot point located along the optical axis between the cornea of the eye and the first lens.

8. The method of claim 7, wherein the cornea has a corneal focal length and the pivot point is located at a distance of approximately one corneal focal length from the cornea.

9. The method of claim 7, wherein the scanning mirror arrangement comprises a single scanning mirror configured to scan in both the x direction and the y direction.

10. The method of claim 7, wherein the scanning mirror arrangement comprises a first scanning mirror configured to scan in an x direction and a second scanning mirror configured to scan in a y direction which is orthogonal to the x direction.

11. The method of claim 7, wherein the optical system includes a beamsplitter disposed in the optical path between the first lens and the second lens, and wherein the beamsplitter is configured to couple light to and from the eye and at least one of a corneal topographer and a wavefront aberrometer.

12. The method of claim 7, wherein the pivot point is located at a distance of approximately 25 millimeters from the cornea.

13. The method of claim 1, further comprising:
causing the eye to gaze at a plurality of different gaze angles over a time period by means of a fixation target;
repeating the directing, controlling, and returning for each of the plurality of different gaze angles such that a total scanned region of the retina has a diameter of at least approximately 6 mm; and
determining the at least one retinal characteristic of the eye from the returned sample light from the retina of the eye for all of the different gaze angles over the total scanned region of the retina.

14. The method of claim 1, wherein the optical system includes:
a first lens having a first focal length, the first lens being disposed along an optical axis along an optical path from a light output point of the scanning mirror arrangement to the eye, and a second lens disposed along the optical path between the first lens and the light output point of the scanning mirror arrangement, the second lens being arranged to receive the sample beam from the scanning mirror arrangement and provide the sample beam to the first lens as a converging beam such that, for all of the plurality of different angles, the sample beam leaves the first lens toward the eye along a path which passes through a pivot point located along the optical axis behind the eye.

15. The method of claim 14, wherein the cornea has a corneal focal length and the pivot point is located at a distance from the cornea of approximately 2.4 times the corneal focal length.

16. The method of claim 14, wherein the pivot point is located at a distance of approximately 60 millimeters behind the cornea.

* * * * *